United States Patent

Avendano et al.

[11] Patent Number: 5,605,905
[45] Date of Patent: Feb. 25, 1997

[54] ANTITUMORAL COMPOUNDS

[75] Inventors: Carmen Avendano; Miguel A. Alonso; Modesta Espada; Dolores Garcia-Gravalos; Jose C. Mendendez; Blanca Ocana; Jose M. Perez, all of Madrid, Spain

[73] Assignee: Universidad Complutense de Madrid, Madrid, Spain

[21] Appl. No.: 412,983

[22] Filed: Mar. 28, 1995

Related U.S. Application Data

[63] Continuation of Ser. No. 73,109, Jun. 4, 1993, abandoned.

[30] Foreign Application Priority Data

Jun. 5, 1992 [GB] United Kingdom ............ 9212000

[51] Int. Cl.⁶ .............. A61K 31/44; C07D 471/06
[52] U.S. Cl. .............. 514/292; 514/297; 546/81; 546/103
[58] Field of Search ............... 514/292, 297; 546/81, 103

[56] References Cited

PUBLICATIONS

Gesto et al. "Synthesis and biological activity of new 1,8–diaza–2,9,10–anthacenetrione derivatives" J. Phar. Sci. v.81 (8) 815–816 (1992).

Lee et al. "Total synthesis of 4–acetyloxymethyl–1,6,9–trimethyl–1,9–diazaanthrac ene–2,5,8,10–tetraone" Tetrahedron Lett. v.31(31)4405–4408 (1990).

Goulart et al. "Azaflurorenones and azaanthrazuinone from Guatteria dielsiana" CA 105:168866x (1986).

Gesto et al. "Synthesis of diaza–anthraquinones by hetero diels–alder cycloaddition reaction" Tetrahedron v.45 4477–4484 (1989).

Primary Examiner—Ceila Chang
Attorney, Agent, or Firm—Ernest V. Linek

[57] ABSTRACT

Azaanthracene-triones of the formula:

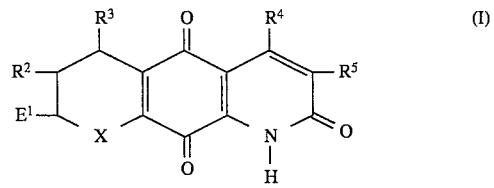

(in which:

$R^1$, $R^2$, $R^4$ and $R^5$ are the same or are different and each is a hydrogen atom or a lower alkyl group;

$R^3$ is a hydrogen atom, a lower alkyl group, a phenyl group or an amino-substituted phenyl group; and X is a —CH—, =N— or —NH—, whereby the ring containing the group X is a benzene, pyridine or dihydropyridene ring)

have antitumoral activity.

3 Claims, No Drawings

ANTITUMORAL COMPOUNDS

This is a continuation of application Ser. No. 08/073,109 filed on Jun. 4, 1993 now abandoned.

FIELD OF THE INVENTION

This invention relates to antitumoral compounds and to pharmaceutical compositions containing them.

BACKGROUND OF THE INVENTION

Diazaquinomicyn A is a natural 1,8-diazaanthraquinone found during the routine study of secondary metabolites from bacteria. [S. Omura, et. al., J. Antibiotics, 35, 1425 (1982); and S. Omura et. al., Tetrahedron Letters, 24, 3643 (1963)]. It exhibits good activity against Gram positive bacteria, due to its capacity to inhibit the thymidylate synthetase [S. Omura, et. al., J. Antibiotics, 38, 1016 (2985); and M. Murata et. al T. Miyasaka, H. Tanaka, S. Omura, J. Antibiotics, 38, 1025 (1985)]. However, Diazaquinomycine A is inactive as an antitumoral agent.

It has now been found, in accordance with the present invention, that certain azaanthracene-triones, as hereinafter defined, possess antitumoral activity.

SUMMARY OF THE INVENTION

According to the invention, therefore, there are provided azaanthracene triones of the general formula:

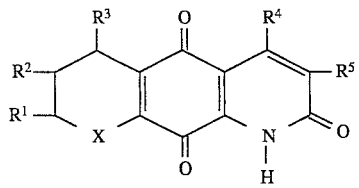

in which:

$R^1$, $R^2$, $R^4$ and $R^5$ are the same or are different and each is a hydrogen atom or a lower ($C_1$–$C_6$) alkyl group;

$R^3$ is a hydrogen atom, a lower ($C_1$–$C_6$) alkyl group, or a phenyl or amino-substituted phenyl group (preferably a dialkylamino substituted phenyl group), at least one of $R^1$, $R^2$, $R^3$, $R^4$ and $R^5$ being other than hydrogen; and X is a group —CH—, =N— or —NH— whereby the ring containing the group X is a benzene, pyridine or dihydropyridene ring, respectively.

DETAILED DESCRIPTION OF THE PREFERRED EMBODIMENTS

The invention also provides pharmaceutical compositions comprising a compound of formula (I) in association with a pharmaceutical carrier or diluent. The invention further provides the use of a compound of formula (I) in the manufacture of an antitumoral composition. Finally, the invention provides a method for the treatment of tumors using compounds of formula (I).

The compounds of formula (I) may be subdivided into three sub-classes, namely:

(i) 5,8-dihydro-1H-1,8-diazaanthracene 2,9,10-triones of the formula:

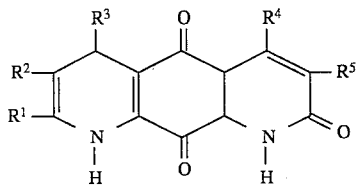

(ii) 1H-1,8-diazaanthracene-2,9,10-triones of the formula:

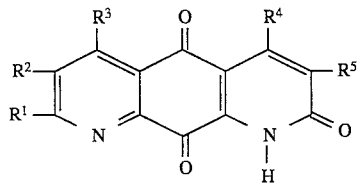

(iii) 1H-1-azaanthracene-2,9,10-triones of the formula:

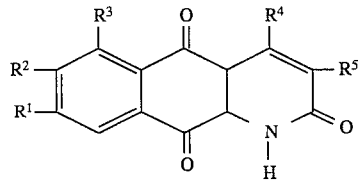

The compounds of formulae (I) may be prepared by Diels-Alder addition of an N,N-dimethylhydrazone of an appropriately substituted alkenal, followed by later treatment if necessary.

Thus, compounds of formulae I(a) and I(b) may be prepared by reaction of a dimethylhydrazone of the formula:

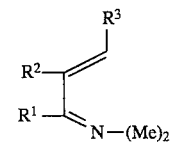

with an azanaphthoquinone of the formula:

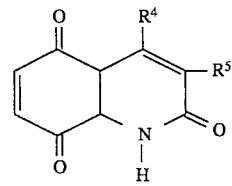

in which case it has been found that reaction may occur to give compounds of formula I(a) or I(b) depending on the nature of the dimethylhydrazone. Compounds of formula I(a) may be converted to compounds of formula I(b) by oxidation.

Compounds of formula I(c) may be prepared by reaction of a dimethylhydrazone of the formula:

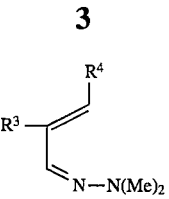

with a naphthaquinone of the formula:

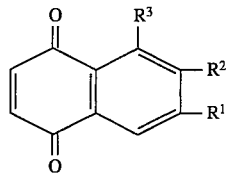

followed by conversion of the resulting azaanthraquinone to its N-oxide and subsequent conversion of this (by reaction with benzoyl chloride and water) to the desired trione.

The starting materials are known or may be prepared using well-established technique.

Thus, for example the dienophile, 4-methyl-(1H)-quinoline-2,5,8-trione, may be obtained by acetoacetylation of 2,5-dimethoxyaniline with 2,2,6-trimethyl-4H-1,3-dioxin-4-one, followed by Knorr cyclization with sulfuric acid, demethylation with hydrobromic acid and oxidation with potassium dichromate in an acidic medium. The starting dienophile, 3-ethyl-1H-quinoline-2,5,8-trione, may be obtained through Vilsmeier-Haack formylation of 2,5-dimethoxybutyranilide, followed by acidic hydrolysis and oxidative demethylation with cerium ammonium nitrate.

Diels-Alder reaction between these dienophiles and N,N-dimethylhydrazones (Helv. Chim Acta, 71, 486) of 2-butenal, 2-methyl-2-pentenal, 3-phenyl-2-propenal, or 3-(4-dimethylamino-phenyl)-2-propenal affords the partially oxidized 3,8-dihydro adducts. The same reaction, when conducted on dimethylhydrazones of 2-methylpropenal and 2-ethylpropenal, gives aromatized adducts. In all cases, the Diels-Alder adducts are accompanied by secondary products formed in the addition of dimethylamine to the $C_6$ position of the starting quinone. The dihydro derivatives may be oxidized by air in refluxing xylene to the corresponding aromatic compounds.

The Diels-Alder reaction of the N,N-dimethylhydrazone of 2-methyl-2-propenal with naphthaquinone gives 3-methyl-1-azaanthraquinone; this compound is then N-oxidized with $H_2O_2/F_3C-CO_2H$, followed by treatment with benzoyl chloride and water to give the compound of formula I(c).

In order that the invention my be well understood the following Examples are given by way of illustration only.

Melting points are uncorrected, and were determined in open capillary tubes, using a Buchi immersion apparatus. Combustion elemental analyses were obtained using a Perkin Elmer 2400 CHN analyzer. Spectroscopic data were obtained with the following instruments: IR, Perkin Elmer 577 and Buck Scientific 500; NMR, Varian VXR-300 (300 MHz for $^1H$ and 75 MHz for $^{13}C$) and Bruker Ac-250 MHz for $^1H$ and 63 MHz for $^{13}C$). The assignments indicated with * and ** can be interchanged.

EXAMPLE 1

Synthesis of 4,6-dimethyl-5-5,8-dihydro-1H-1,8-diazaanthracene-2,9,10-trione (1)

To a solution of 4-methyl-1H-quinoline-2,5,8-trione (196) mg, 1 mmol) in dry chloroform (130 ml) under nitrogen was added 159 mg (1.14 mmol) of 2-methyl-2-pentenal dimethylhydrazone. The solution was stirred at room temperature for 5 minutes. After evaporation of the solvent, the residue was purified by column chromatography on silica gel, eluting with dichloromethane/ethyl acetate (6:4) to give 33 mg of unreacted hydrazone, 133 mg (45%) of 1 and 105 mg of 6-dimethylamino-4-metlhyl-1H-quinoline-1,5,8-trione.

Melting point: 220°–223° C.

IR(KBr): 3640–3060 (N—H); 1650 (C=O) $cm^{-1}$.

$^1H$-NMR (300 MHz, $CDCl_3$) δ 6.65 (m, 2H, $C_3$—H and $N_8$—H); 6.10 (dd, 1H, $J_{7,8}$=4.5 Hz and J=1.2 Hz, $C_7$—H): 3.65 (t, 1H, J=4.5 Hz, $C_5$—H); 2.62 (d, 3H, J=1.2 Hz, $C_4$—$CH_3$); 1.73 (d, 3H, J=1.2 Hz, $C_6$—$CH_3$); 1.56 (dq, 2H, J=7.5 and 4.5 Hz, $C_5$—$CH_2$—$CH_3$); 0.81 (t, 3H, J=7.5 Hz, $C_5$—$CH_2$—$CH_3$) ppm.

$^{13}C$-NMR (75.4 MHz, $CDCl_3$) δ 183.08 ($C_9$); 175.79 ($C_{10}$); 160.83 ($C_2$); 152.03 ($C_4$); 137.11 ($C_{8a}$)*; 136.33 ($C_{9a}$)*; 127.76 ($C_3$); 119.49 ($C_7$); 115.46 ($C_6$); 114.93 ($C_{4a}$); 111.51 ($C_{10a}$); 36.43 ($C_5$); 25.46 ($C_5$—$CH_2$—$CH_3$); 22.53 ($C_4$—$CH_3$); 18.68 ($C_6$—$CH_3$); 9.27 ($C_5$—$CH_2$—$CH_3$) ppm.

EXAMPLE 2

Synthesis of 4-methyl-5-phenyl-5,8-dihydro-1H-1,8-diazaanthracene-2,9,10-trione (2)

A solution of 233 mg (1.34 mmol) of trans-cinnamaldehyde N,N-dimethylhydrazone was added to a solution of 4-methyl-1H-quinoline-2,5,8-trione (127 mg, 0.67 mmol) in dry chloroform (120 ml). The reaction was stirred under nitrogen at room temperature for 3 days, with periodical additions of solvent (100 ml each 12 h). A further amount of 166 mg (0.61 mmol) of the hydrazone was added, and the reaction was refluxed for 24 h and evaporated to dryness, and the residue was purified by silica gel chromatography using a gradient elution, starting with neat dichloromethane to dichloromethane/ethyl acetate (7:3), to yield 204 mg of the starting diene, 72 mg (35%) of 2 and 160 mg of 6-dimethylamino-4-methyl-1H-quinoline-2,5,8-trione.

Melting point, 206° C.

IR (KBr): 3400 (NH), 1660, 1655, 1600 (C=O) $cm^{-1}$.

$^1H$-NMR (300 MHz, $d_5$-pyridine) δ: 10.40 (d, 1H, J=4.0 Hz, N8—H); 7.69 (dd, 2H, $J_{2', 3}$=8.0 Hz, $J_{2', 4}$=1.0 Hz, $C_2$—H, $C_6$—H); 7.41 (t, 2H, J=8.0 Hz, $C_3$—H, $C_5$—H); 7.25 (tt, $J_{4', 3}$=7.8 Hz, $J_{4', 2}$=1.1 Hz, $C_4$—H); 6.70 (m, 2H, $C_3$—H, $C_7$—H); 5.17 (m, 1H, $C_6$—H); 5.11 (d, 1H, J=5.0 Hz, $C_5$—H), 2.46 (d, 3H, J=1.0 Hz, $C_4$—$CH_3$) ppm.

EXAMPLE 3

Synthesis of 5-(4-Dimethylamino-phenyl) 4-methyl-5,8-dihydro-1H-1,8-diazaanthracene-2,9,10-trione (3).

A solution of 41.5 mg (2.2 mmol) of 4-methyl-1H-quinoline-2,5,8-trione in dry chloroform (130 ml) and 524 mg (2.4 mmol) of N,N-dimethylhydrazone of p-dimethylaminocinnamaldehyde was stirred under reflux during four days. After evaporation of the solvent, the residue was purified by silica gel chromatography using gradient elution from dichloromethane to dichloromethane/ethyl acetate (7:3), to yield 80 mg (11%) of 3 and 313 mg of 6-dimethylamino-4-methyl-1H-quinoline-2,5,8-trione.

Melting point: 252°–256° C.

IR (KBr): 3630–3100 (NH), 1650, 1640, 1635 (C=O) cm$^{-1}$.

$^1$H-NMR (300 MHz, d$_5$-pyridine) δ 10.24 (d, 1H, J=3.0 Hz, N8—H); 7.62 (d, 2H, J=8.8 Hz, C$_2$'—H, C$_6$'—H); 6.85 (d, 2H, J=8.8 Hz, C$_3$'—H, C$_5$'—H); 6.76 (m, C$_7$—H); 6.74 (s, 1H, C$_3$—H); 2.78 (s, 6H, N(CH$_3$)$_2$); 2.54 (s, 3H, C$_4$—CH$_3$) ppm. (The signal of C$_6$—H is included in the water signal).

EXAMPLE 4

Synthesis of 4,5-dimethyl-1H-1,8-diazaanthracene-2,9,10-trione (4)

a) A solution of 1.45 mg (0.76 mmol) of 4-methyl-1H-quinoline-2,5,8-trione in dry chloroform (130 ml) and 85 mg (0.76 mmol) of dimethylhydrazone of crotonaldehyde was stirred at room temperature for five minutes. After evaporation of the solvent, the residue was purified by silica gel chromatography, using a gradient elution from dichloromethane to dichloromethane/ethyl acetate (6:4), to yield 100 mg (51%) of 4,5-dimethyl-5,8-dihydro-1H-1,8-diazaanthracene-2,9,10-trione(4), 43 mg of the starting hydrazone and 62 mg of 6-dimethylamino-4-methyl-1H-quinoline-2,5,8-trione.
Melting point: 301°–303° C.
IR (KBr): 3660–3040 (N—H); 1660, 1650 (C=O) cm$^{-1}$.
1N-NMR (300 MHz, d$_6$-DMSO) δ: 8.77 (d, 1H, J=3.6 Hz, N$_8$—H); 6.54 (d, 1H, J—1.2 Hz, C$_3$—H); 6.14 (dd, 1H, J$_{7,8}$=4.0 Hz, J$_{7,6}$=7.8 Hz, C$_7$—H); 4.85 (m, 1H, C$_6$—H); 3.50 (m, 1H, C$_5$—H); 2.55 (s, 3H, C$_4$—CH$_3$); 1.02 (d, 3H, J=3.6 Hz, C$_5$—CH$_3$) ppm.

b) A solution of 80 mg (0.31 mmol) of 4,5-dimethyl-5,8-dihydro-1H-1,8-diazaanthracene-2,9,19-trione in xylene (60 ml) was refluxed for 58 hours, while air was bubbled through it. After evaporation of the solvent the residue was purified by silica gel chromatography using ethyl acetate as eluent, to yield 75 mg (95%) of 4.
Melting point: 258°–261° C. (ethyl acetate)
IR (KBr): 3440 (NH); 1655 (C=O) cm$^{-1}$.
$^1$H-NMR (300 MHz, CDCl$_3$) δ: 8.85 (d, 1H, J=5.1 Hz, C$_7$—H); 7.53 (d, 1H, J=4.8 Hz, C$_6$—H); 6.72 (d, 1H, J=1.2 Hz, C$_3$—H); 2.86 (s, 3H, C$_5$—CH$_3$); 2.68 (d, 3H, J=1.2 Hz, C$_4$—CH$_3$) ppm.
$^{13}$C-NMR (75.4 MHz, CDCl$_3$) δ 160.45 ($_{8a}$); 153.31 (C$_7$): 152.02 (C$_5$); 151.58 (C$_4$; 147.21 (C$_{9a}$; 132.81 (C$_6$; 129.26 (C$_{10a}$); 128.78 (C$_3$); 119.24 (C$_{4a}$); 29.26 (C$_5$—CH$_3$); 22.82 (C$_4$—CH$_3$) ppm.

EXAMPLE 5

Synthesis of 6-ethy-4-methyl-1H-1,8-diazaanthracene-2,9,10-trione (5)

A solution of 150 mg (0.9 mmol) of 4-methyl-1H-quinoline-2,5,8-trione and 150 mg (0.79 mmol) of 2-ethylacrolein dimethylhydrazone in dry chloroform (130 ml) was stirred at room temperature for five minutes. After evaporation of the solvent, the residue was purified by silica gel chromatography using ethyl acetate as eluent to yield 29 mg of the starting hydrazone, 64 mg (30%) of 5 and 60 mg of 6-dimethylamino-4-methyl-1H-quinoline-2,5,8-trone.
Melting point: 225°–227° C. (ethyl acetate).
IR (KBr): 3420 (N—H); 1656, 1636 (C=O) cm$^{-1}$.

$^1$H-NMR (300 MHz, CDCl$_3$): δ 9.78 (bs, 1H, N—H); 8.90 (s, 1H); 2.89 (q, 2H, J=9.1 Hz, C$_6$—CH$_2$—CH$_3$): 2.71 (s, 3H, C$_4$—CH$_3$; 1.38 (t, 3H, J=9.1 Hz, C$_6$—CH$_2$—CH$_3$) ppm.
$_{13}$C-NMR (75 MHz, CDCl$_3$) δ: 180.93 (C$_9$); 176.30 (C$_{10}$; 171.19 (C$_2$); 160.06 (C$_{8a}$); 154.89 (C$_7$); 151.78 (C$_4$); 146.47 (C$_6$); 140.14 (C$_{9a}$); 133.92 (C$_5$; 130.51 (C$_{10a}$); 128.07 (C$_3$); 115.16 (C$_{4a}$); 26.59 (CH$_2$—CH$_3$); 21.07 (C$_4$—CH$_3$); 14.20 (CH$_2$—CH$_3$) ppm.

EXAMPLE 6

Synthesis of 5-(p-dimethylaminophenyl)-4-methyl-1H-1,8-diazaanthracene-2,9,10-trione (6)

A solution of 25 mg (0.07 mmol) of 3 in xylene (60 ml) was refluxed for 16 hours while air was bubbling through the solution. After evaporation of the solvent, the residue was purified by silica gel chromatography, using ethyl acetate as eluent to yield 20 mg (80%) of 6.
Melting point: 305°–309° C. (ethyl acetate)
IR (KBr): 3650–3080 (N—H; 1676, 1664, 1656 (C=O) cm$^{-1}$.
$^1$H-NMR (300 MHz, CDCl$_3$) δ 8.88 (d, 1H, J=4.8 Hz, C$_7$—H); 7.56 (d, 1H, J=4.8 Hz, C$_6$—H); 7.22 (d, 2H, J=8.8 Hz, C$_2$'H and C$_6$'—H); 6.77 (d, 2H, J=8.6 Hz, C$_3$'—H and C$_5$'—H); 6.70 (d, 1H, J=1.2 Hz, C$_3$—H); 3.06 (s, 6H, N(CH$_3$)$_2$); 2.56 (d, 3H, J=1.2 Hz, C$_4$—CH$_3$) ppm.
$_{13}$C-NMR (63, Mhz, CDCl$_3$) δ 182.21 (C$_9$); 177.14 (C$_{10}$); 167.94 (C$_2$); 160.39 (C$_{8a}$); 152.90 (C$_7$); 151.68 (C$_5$); 150.89 (C$_4$); 147.59 (C$_{4'}$); 132.58 (C$_{6*}$); 131.06 (C$_{1'*}$); 129.56 (C$_{2'}$ and C$_{6'}$); 128.96 (C$_{3}$); 128.58 (C$_{10a}$); 117.51 (C$_{4a}$); 111.84 (C$_{3'}$ and C$_{5'}$); 40.35 (N(CH$_3$)2); 22.56 (C$_4$—CH$_3$) ppm.

EXAMPLE 7

Synthesis of 3-ethyl-6-methyl-1H-1,8-diazaanthracene-2,9,10-trione (7)

a) To a cooled solution of 2,5-dimethoxyaniline (1 g, 0.65 mmol) in dry benzene (7 ml). The reaction was stirred at room temperature for 1 h and was then quenched with cold 25% aqueous sodium carbonate (10 ml). After vigorously stirring the two-phase system for 30 min, the benzene layer was separated and the aqueous phase was extracted with ethyl ether (3×50 ml). The combined organic layers were dried over sodium sulphate and evaporated, and the residue (7) was crystallized from petroleum ether, Yield, 86%.
Melting point: 34° C. (petroleum ether)
Ir (KBr): 3235 (NH); 1660(C=O); 1235 (OCH$_3$) cm$^{-1}$.
$^1$H-NMR (300 MHzm, CDCl$_3$) δ: 8.10 (d, 1H, J=3.0 Hz, C$_6$—H); 7.80 (s, 1H, NH); 6.70 (d, 1H, J=7.5 Hz, C$_3$—H); 6.50 (dd, 1H, J=7.5 and 3.0 Hz, C$_4$—H); 3.80 (s, 3H, C$_5$—OCH$_3$); 3.70 (s, 3H, C$_2$—OCH$_3$); 2.40 (c, 3H, J=7.5 Hz, C$_2$—H); 1.20 (t, 3H, J=7.5 Hz, C$_3$—H) ppm.
$^{13}$C-NMR (75.4 MHz, CDCl$_3$) δ: 171/87 (C$_1$); 153.80 (C$_{5'}$); 141.77 (C$_{2'}$); 128.34 (C$_{1'}$); 110.55 (C$_3$); 108.34 (C$_{4'}$); 105.64 (C$_{6'}$); 56.10 and 55.68 (2 OCH$_3$); 30.98 (C$_2$); 9.55 (C$_3$) ppm.

b) A mixture of phosphorus oxychloride (3 ml, 31.6 mmol) and dimethylformamide (0.52 ml, 6.6 mmol) was stirred at −30° C. for 15 min, while kept in a nitrogen atmosphere. 1 g (4.5 mmol) of N-(2,5-dimethoxyphenyl)butanamide was then added in one portion, and the solution was heated for two hours at 110° C. On completion of the reaction, as monitored by tlc, the solution was poured on crused ice, basified with 25% aqueous ammonium hydroxide and extracted with chloroform (3×50 ml). The organic layers were dried over sodium sulphate and evaporated, and the residue was purified by silica gel chromatography using petroleum ether/ethyl ether (2:1) as eluant, to give 856 mg (75%) of 2-chloro-3-ethyl-5,8-dimethoxyquinoline.

Melting point, 120° C. (ethyl ether-petroleum ether).

Ir (Kbr): 1265 (OCH3) cm$^{-1}$.

$^1$H-NMR (300 MHz, CDCl$_3$) δ: 8.35 (s, 1H, J=8.0 Hz, C$_7$—H); 6.74 (d, 1H, J=8.0 Hz, C$_6$—H); 4.01 (s, 3H, C$_8$—OCH$_3$); 3.95 (s, 3H, C$_5$—OCH$_3$); 2.92 (c, 2H, J=7.5 Hz, CH$_2$—CH$_3$); 1.30 (t, 3H, J=7.5 Hz, CH$_2$—CH$_3$) ppm.

$^{13}$C-NMR (75.4 MHz, CDCl$_3$) δ: 151.34 (C$_2$); 148.39 (C$_{5*}$); 148,08 (C$_{8*}$); 138.29 (C$_{8a}$); 135.30 (C$_3$); 131.43 (C$_4$); 120.84 (C$_{4a}$); 106.99 (C$_7$); 103.97 (C$_6$); 55.65 and 55.91 (2 OCH$_3$); 26.52 (CH$_2$—CH$_3$); 13.44 (CH$_2$—CH$_3$) ppm.

c) A solution of 200 mg (0.92 mmol) of 2-chloro-3-ethyl-5,8-dimethoxyquinoline in acetic acid (3 ml) and water (1 ml) was refluxed for 5 h. After evaporation of the solvent, the residue was dissolved in water, basified with 25% aqueous ammonium hydroxide and extracted with chloroform (3×25 ml). The combined chloroform layers were dried over sodium sulphate and evaporated, yielding 185 mg (100%) of 3-ethyl-5,8-dimethoxy-1H-quinolin-2-one.

Melting point, 160° C. (ethanol).

1R (KBr): 3240–2810 (NH); 1650 (C$_2$=O); 1245 (2 OCH$_3$) cm$^{-1}$.

$^1$H-NMR (250 MHz, CDCl$_3$) δ: 9.18 (s, 1H, C$_4$—H); 6.78 (d, 1H, J=8.7 Hz, C$_7$—H); 6.46 (d, 1H, J=8.7 Hz, C$_6$—H); 3.88 and 3.87 (2s, 6H 2 OCH$_3$); 2/56 (c, 2H, J=9.0 Hz, CH$_2$—CH$_3$); 1.25 (3H, J=9.0 Hz, CH$_2$—CH$_3$) ppm.

$^{13}$C-NMR (63 MHz, CDCl$_3$) δ: 162.10 (C$^2$); 149.25 (C$_5$); 139.45 (C$_8$); 135.11 (C$_{8a}$); 129.83 (C$_4$); 128.19 (C$_3$); 111.14 (C$_{4a}$); 108.94 (C$_7$); 100.95 (C$_6$); 56.08 and 55.67 (2 OCH$_3$); 23.45 (CH$_2$—CH$_3$); 12.64 (CH$_2$—CH$_3$) ppm.

d) Cerium ammonium nitrate (284 mg, 0.5 mmol) was added in small portions to a stirred suspension of 3-ethyl-5,8-dimethoxy-1H-quinolin-2-one(50 mg, 0.2 mmol) in water (0.5 ml) and acetonitrile (1 ml). After 5 minutes at room temperature, water (3 ml) was added and the reaction mixture was extracted with chloroform (3×20 ml), yielding 3-ethyl-1H-quinoline-2,5,8-trione (44 mg, 100 %). The analytical sample was obtained by rapid silica gel chromatography, eluting with ethyl ether.

Melting point 168° C.

IR (KBr): 1650 (C=O) cm.

$^1$H-NMR (300 MHz, CDCl$_3$) δ: 9.60 (s, 1H, NH); 7.75 (s, 1H, C$_4$—H); 6.87 (m, 2H, C$_7$—H and C$_6$—H); 2.66 (c, 2H, J=7.8 Hz, CH$_2$—CH$_3$); 1.26 (t, 3H, J=7.8 Hz, H$_2$—CH$_3$) ppm.

$^{13}$C-NMR (75.4 MHz, CDCl$_3$) δ: 177.92 (cg); 174.79 (C$_5$); 156.81 (C$_2$); 138.98 (C$_{8a}$); 133.50 (C$_6$); 130.57 (C$_3$); 129.96 (C$_7$); 125.33 (C$_4$); 110.39 (C$_{4a}$); 19.17 (CH$_2$—CH$_3$); 7.33 (CH$_2$—CH$_3$) ppm.

e) A suspension of 3-ethyl-1H-quinoline-2,5,8-trione (200 mg, 0.99 mmol) in chloroform (40 ml) is treated with 145 mg (1.3 mmol) of 2-methylpropenal dimethylhydrazone. The reaction was stirred at room temperature for 5 minutes and evaporated, and the residue was chromatographed on silica gel, eluting with ethyl acetate, to yield 120 mg (45%) of 7.

Melting point, 260°–262° C.

$^1$H-NMR (250 MHz, CDCl$_3$) δ: 9.70 (br. s, 1H, NH) 8.95 (s, 1H, C$_7$—H); 8.35 (s, 1H, C$_5$—H); 7.96 (s, 1H, C$_4$—H); 2.63 (q, 2H, J=7.5 Hz, CH$_2$—CH$_3$); 2.60 (s, 3H, C$_6$—CH$_3$); 1.30 (t, 3H, J=7.5 Hz, CH$_2$—CH$_3$) ppm.

$^{13}$C-NMR (63 MHz, CDCl$_3$) δ: 179.91 (C$_9$): 176.20 (C$^{10}$); 171.10 (C$_2$); 161.37 (C$_{8a}$); 155.36 (C$_7$); 144.52 (C$_3$); 140.16 (C$_6$); 137.25 (C$_{9a}$); 134.94 (C$_5$); 130.30 (C$_4$ and C$_{10a}$); 129.35 (C$_3$); 116.26 (C$_{4a}$); 23.93 (C$_6$—CH$_3$); 12.01 (C$_3$—CH$_2$—CH$_3$) ppm.

EXAMPLE 8

Synthesis of 3-Methyl-1H-1azaanthracene-2,9,10-trione (8)

a) A solution of 30-methyl-1-azaanthraquinone (1 g, 4 mmol) in trifluoroacetic acid (6 ml) was treated with percarbamide (0.63 g) and stirred at room temperature for 24 h, with hourly additions of 315 mg of percarbamide up to a total amount of 1.58. The solution was stirred for 24 hours. The addition of ethyl acetate (6 ml) gave an orange solid which was washed with water to afford 0.89 g (83%) of 3-methyl-1-azaanthracenequinone-1-oxide. Crystallization from ethyl acetate/ethanol (9:1) yielded 0.54 of orange needles.

Melting point could not be obtained, as the N-oxide decomposed on heating.

IR (KBr): 1680 (O—O) cm$^{-1}$.

$^1$H-NMR (250 MHz, CDCl$_3$) δ: 8.41 (s, 1H, C$_2$—H); 8.37 (dd, 1H, J$_{5-6}$=1.21 Hz, C$_5$—H); 8.24 (dd 1H, J$_{8-7}$=7.3 Hz, J$_{8-6}$=1.71 Hz, C$_8$—H); 7.95 (s, 1H, C$_4$—H); 7.84 (m, 2H, C$_6$—H and C$_7$—H); 2.46 (s, 3H, CH$_3$) ppm.

b) To a solution of the N-oxide (125 mg, 0.523 mmol) in amylene-stabilized chloroform (12 ml) were added three portions of 0.1 ml (2.5 mmol) of benzoyl chloride in ½ hour intervals. The solution was stirred at 60° C. for 3 h, and was then treated with water (0.4 ml) and kept at 60° C. for 1 h and for further 12 h at room temperature. The precipitated yellow solid was filtered and washed with ethyl ether and petroleum ether, yielding 80 mg (64%) of 8.

Melting point>300° C.

IR (KBr): 3640–3300 (NH); 1680, 1670, 1640 (C=O) cm$^{-1}$.

$^1$H-NMR (300 MHz, CDCl$_3$) δ: 8.25 (dd, 1H, J$_{7-8}$=7.3, J$_{8-6}$=1.47 Hz, C$_8$—H); 8.20 (dd, 1H, J$_{5-6}$=7.3 Hz, J$_{5-7}$=1.47 Hz, C$_5$—H); 8.00 (q, 1H, J=1.20 Hz, C$_4$—H); 7.82 (m, 1H, C$_6$—H and C$_7$—H); 2.31 (d, 3H, J=1.20 Hz, CH$_3$) ppm.

BIOLOGICAL ACTIVITY

Compounds were diluted in DMSO/MeOH/Acetone (1:4.5:4.5) and they were tested at different concentrations. The solvent was allowed to evaporate before the cells were seeded.

The following antitumoral assay, employing the current screening protocol has been carried out using the following cell line:

P-388 (lymphoid neoplasm from DBA/2 mouse).

Assay Against P-388 Cells (Lymphoidneoplasm from DBA/2 Mouse )

P-388 cells were seeded into 16 mm wells at $1\times10^4$ cells per well in 1 ml aliquots of MEM 10C containing different concentrations of the compound. All determinations were carried out in triplicate. A separate set of cultures without drug was counted daily to ensure that the cells remained in exponential growth over the period of observation. After three days of incubation, cells were counted and the $IC_{50}$ was determined.

| COMPOUNDS | $IC_{50}$ µg/ml |
|---|---|
| 1 | 1 |
| 2 | 0.25 |
| 3 | 20 |
| 4 | 1 |
| 5 | 0.5 |
| 6 | 1 |
| 7 | 0.2 |
| 8 | 0.2 |

What is claimed is:

1. The diazaquinomicin analog represented by the following structure:

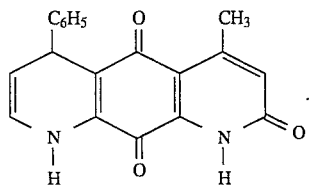

2. An antiumoral pharmaceutical composition comprising the compound of claim 1 and a pharmaceutically acceptable carrier or diluent.

3. A method of inhibiting the growth of mammalian tumor cells comprising administering to said mammalian cells an effective growth inhibiting amount of the compound of claim 1, and wherein said tumor cells are lymphoid neoplasm cells.

* * * * *